(12) United States Patent
Scarpellini

(10) Patent No.: US 8,734,014 B2
(45) Date of Patent: May 27, 2014

(54) RADIOLOGICAL APPARATUS

(75) Inventor: Luciano Scarpellini, Cavernago (IT)

(73) Assignee: General Medical Merate S.p.A., Seriate (IT)

( * ) Notice: Subject to any disclaimer, the term of this patent is extended or adjusted under 35 U.S.C. 154(b) by 296 days.

(21) Appl. No.: 13/254,377

(22) PCT Filed: Mar. 5, 2010

(86) PCT No.: PCT/IB2010/050960
§ 371 (c)(1),
(2), (4) Date: Sep. 1, 2011

(87) PCT Pub. No.: WO2010/100625
PCT Pub. Date: Sep. 10, 2010

(65) Prior Publication Data
US 2011/0317811 A1    Dec. 29, 2011

(30) Foreign Application Priority Data

Mar. 5, 2009   (IT) .................................. MI09A0318

(51) Int. Cl.
*H05G 1/02* (2006.01)
(52) U.S. Cl.
USPC .............................. 378/197; 378/209; 378/62

(58) Field of Classification Search
USPC ..................... 378/62, 193–197, 209
See application file for complete search history.

(56) References Cited

U.S. PATENT DOCUMENTS

| 5,014,292 A | 5/1991 | Siczek et al. |
| 5,930,328 A * | 7/1999 | Nakamura et al. .............. 378/91 |
| 2005/0234327 A1 | 10/2005 | Saracen et al. |

FOREIGN PATENT DOCUMENTS

| DE | 19927480 | 1/2001 |
| DE | 10241189 | 3/2004 |
| EP | 0368067 | 5/1990 |

* cited by examiner

*Primary Examiner* — Courtney Thomas
(74) *Attorney, Agent, or Firm* — Brannen Law Office, LLC

(57) ABSTRACT

The present invention relates to a radiological apparatus (1) comprising a base (2) adapted to stand on a floor, a column-shaped chassis (3) mounted on the base, a column-shaped stand (4) mounted on the chassis, a patient bed (5) mounted on the chassis, an X-ray detector (6) mounted on the chassis, a slide (7) mounted on the stand, an arm (8) mounted on the slide, an X-ray emitter (9) mounted on the arm; the axis of the chassis column and the axis of the stand column are perpendicular to one another; the apparatus comprises further mechanisms adapted to implement a plurality of movements between its parts (2, 3, 4, 5, 6, 7, 8, 9) so as to achieve a highly flexible functionality sufficient to meet a variety of clinical and diagnostic needs.

12 Claims, 5 Drawing Sheets

RADIOLOGICAL APPARATUS

This application is being filed in the United States for the national phase of international application number PCT/IB2010/050960 filed on 5 Mar. 2010 (publication number WO 2010/100625 A1), claiming priority on prior application MI2009A000318 filed in Italy on 5 Mar. 2009, the contents of each being hereby incorporated herein by reference.

DESCRIPTION

1. Field of the Invention

The present invention relates to a radiological apparatus.

The present invention consequently refers to an apparatus suitable for conducting diagnostic investigations in patients with the aid of X-rays.

2. State of the Art

Various types of radiological apparatus have been known for a very long time.

An apparatus for conducting radiographic examinations always comprises an X-ray emitter (generally a radiogenic tube) and an X-ray detector (generally, a cassette holder in the past and, more recently, increasingly frequently a static or dynamic digital image detector). Moreover, there is almost always a patient bed on which the patient lies, where necessary, while the X-ray is taken.

The types of apparatus available on the market have a limited use, covering one or a few specific clinical and diagnostic needs.

It would consequently be very useful to have an apparatus available that is readily adaptable to numerous different clinical and diagnostic needs.

SUMMARY OF THE INVENTION

The general object of the present invention is to provide a radiological apparatus that is far more versatile than the known art.

Specific objects of the present invention include providing a radiological apparatus that has a straightforward and economical structure and that is simple, quick and economical to operate.

These objects are achieved by the radiological apparatus with the features set out in the claims attached to the present description and that form an integral part thereof.

BRIEF DESCRIPTION OF THE FIGURES

The present invention will become clear from the description that follows, with reference to the attached drawings, wherein.

Figure 1:
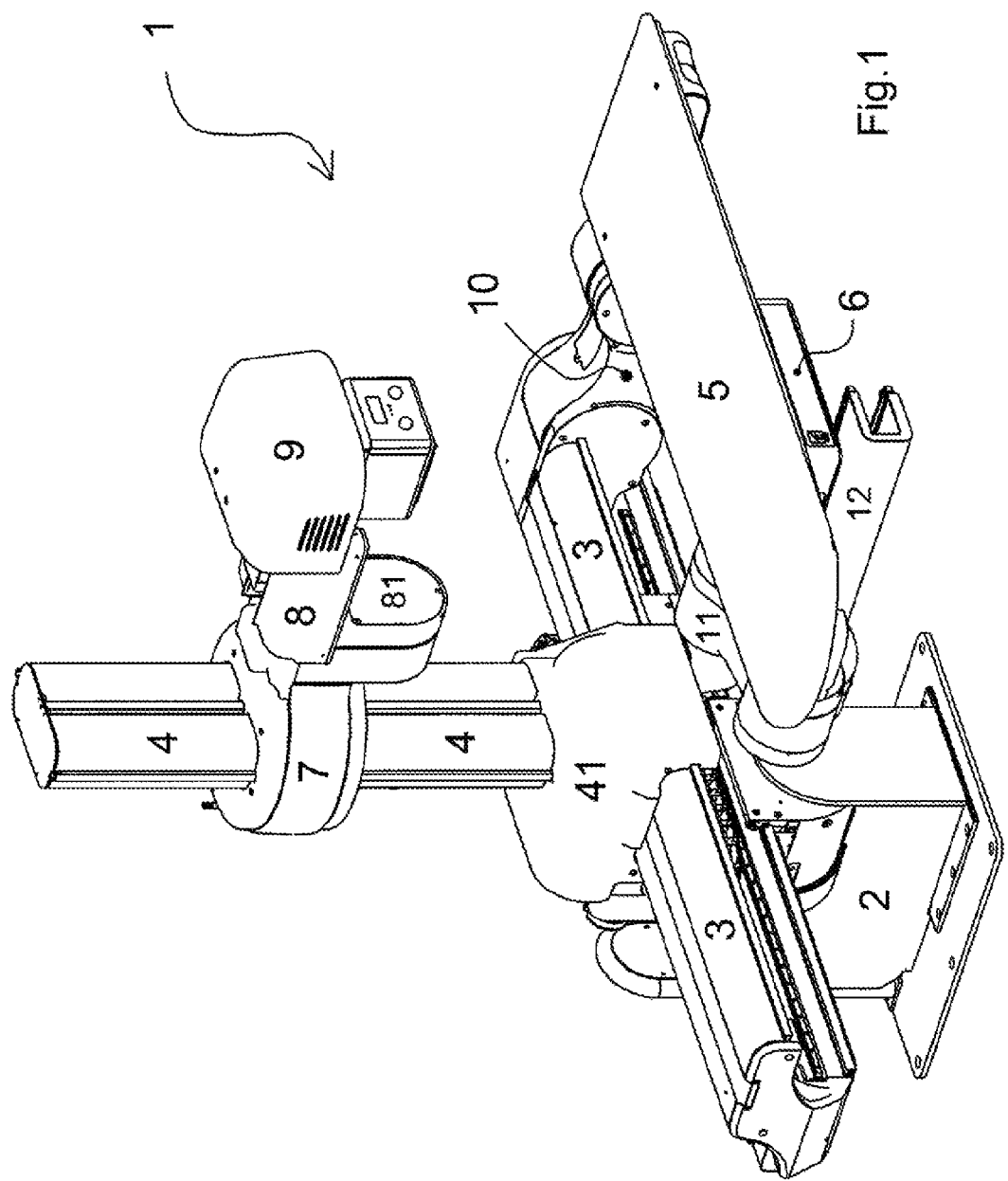
FIG. 1 is a perspective view from the front of one embodiment of the radiological apparatus according to the present invention in a first operating condition.

Both said description and said drawings shall be considered only as a non-limiting example.

DETAILED DESCRIPTION OF THE INVENTION

In the attached figures, which all refer to the same embodiment of the radiological apparatus according to the present invention, the numeral 1 indicates the apparatus as a whole.

The essential mechanical components of the apparatus 1 include: a base 2, a chassis 3, a stand 4, a patient bed 5, an X-ray detector 6, a slide 7, an arm 8, and an X-ray emitter 9.

The base 2 is adapted to stand on the floor.

The chassis 3 is in the shape of a column and is mounted directly and rotatably on the base 2.

The stand 4 is in the shape of a column and is mounted directly and translatably on the chassis 3; its translation is achieved by means of a slide 41 on the stand 4 (situated at one end of the latter).

The patient bed 5 is mounted indirectly and translatably on the chassis 3.

The X-ray detector 6 is mounted indirectly and both translatably and rotatably on the chassis 3.

The slide 7 is mounted directly and translatably on the stand 4.

The arm 8 is mounted indirectly and rotatably on the slide 7.

The X-ray emitter 9 is mounted directly and translatably on the arm 8.

In the example shown in the figures, the axis of the chassis column 3 and the axis of the stand column 4 are perpendicular to one another.

The apparatus 1 also comprises the following important mechanical components: an arm 10 associated with the patient bed, as well as an arm 11, a shaft 12 and a slide 13, all associated with the X-ray detector 6.

As concerns the patient bed 5, this is mounted directly (and rotatably) on the arm 10, which is mounted directly (and rotatably) on the chassis 3; these two rotations are achieved (and coordinated) so that the patient bed 5 is always parallel to itself and can consequently only perform translations.

As for the X-ray detector 6, this is mounted directly (and rotatably) on the slide 13, which is mounted directly (and translatably) on the shaft 12, which in turn is mounted directly (and both translatably and rotatably) on the chassis 3; these two rotations can be achieved (and coordinated) so that the detector 6 remains parallel during any movement and consequently performs a simple translatory movement.

The apparatus 1 has a structure such that the arm 10 and the arm 11 rotate in two planes (or, to be more precise, in two vertical strips of space) perpendicular to one another; the arm 11 rotates in a vertical strip of space that lies alongside the patient bed 5 (in particular between the patient bed 5 and the chassis 3) and there is no risk of these two parts interfering with one another.

Figure 4:
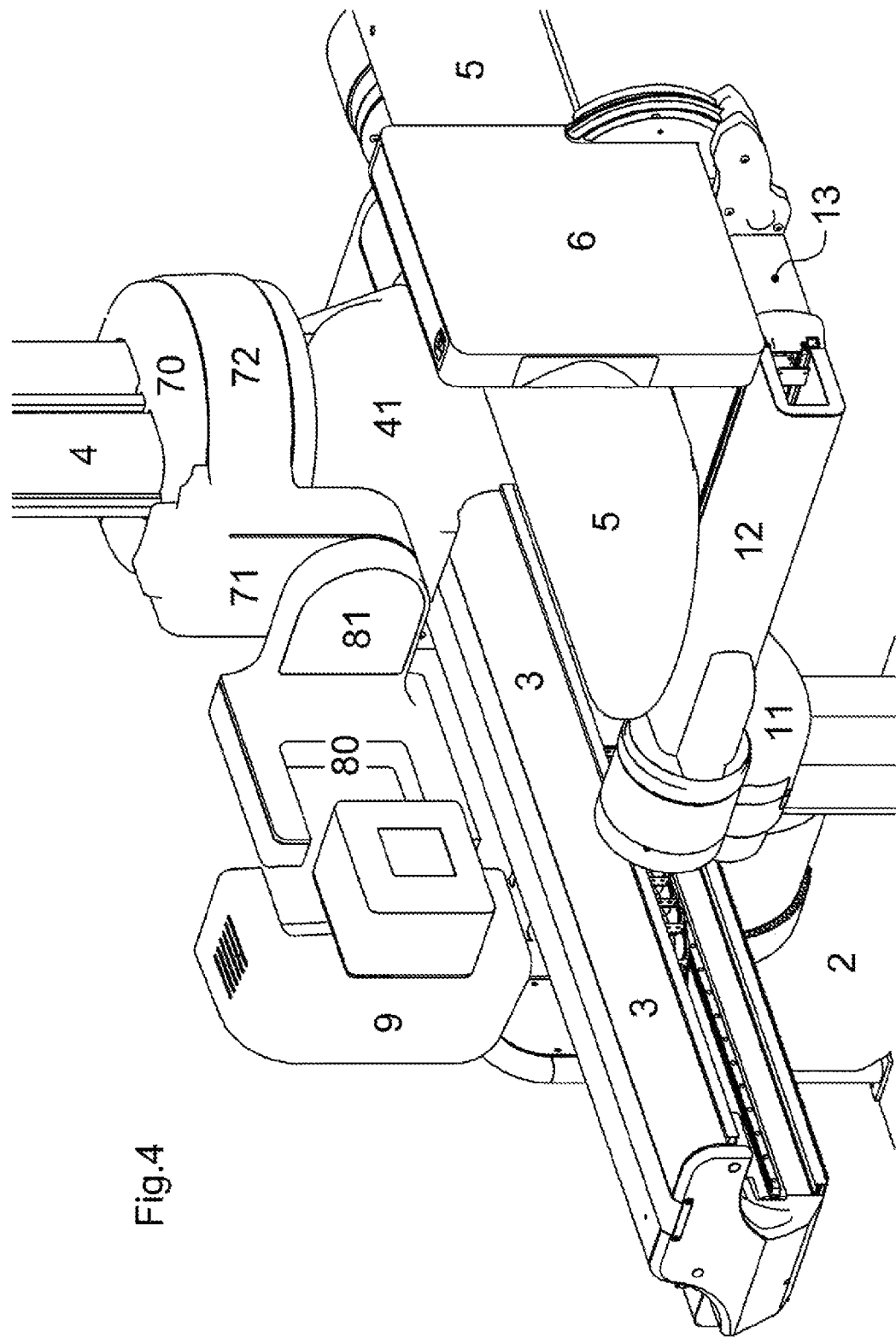
FIG. 4 is a detail of a perspective view from the front of one embodiment of the radiological apparatus according to the present invention in a fourth operating condition.

As shown particularly in FIG. 4, the slide 7 comprises a cylindrical body 70 with an axial through hole; the slide 7 is inserted on the stand 4 by means of this hole and it can translate thereon (the body 70 and the stand 4 are consequently coaxial); the slide 7 also comprises a movable element consisting of a large ring 72 and an appendage 71 extending from the ring 72 in a direction parallel to the axis of the body 70; the movable element is mounted on the body 70 so that it can rotate around the body about an axis of rotation that coincides with the axis of the body 70.

As shown particularly in FIG. 4, the arm 8 comprises a body 80 with a parallelepiped shape that extends in a direction perpendicular to the axis of the stand 4, and an appendage 81 that extends from the body 80 in a direction perpendicular thereto.

The appendages 71 and 81 are hinged to one another at the ends; the arm 8 can thus rotate in relation to the slide 7; in addition, the arm 8 always maintains a direction orthogonal to the axis of the body 70 and consequently of the stand 4.

The X-ray emitter 9 is mounted directly on the body 80 of the arm 8 so that it can translate in a direction parallel to the direction in which said body extends.

It may be advantageous to make the arm 8 in the shape of a large, robust fork designed to make the emitter 9 slide inside it, e.g. by means of two parallel rails, each fixed to one of the two elongated members of the fork; a shell may also be provided, attached to the fork and surrounding the emitter, while leaving it free to slide therein.

The above-mentioned (direct and indirect) assemblies are designed to enable reciprocal movements between these mechanical components; in fact, the apparatus 1 comprises mechanisms designed to achieve a plurality of movements between its parts.

There are twelve allowable movements, which are listed and explained below.

Figure 3:
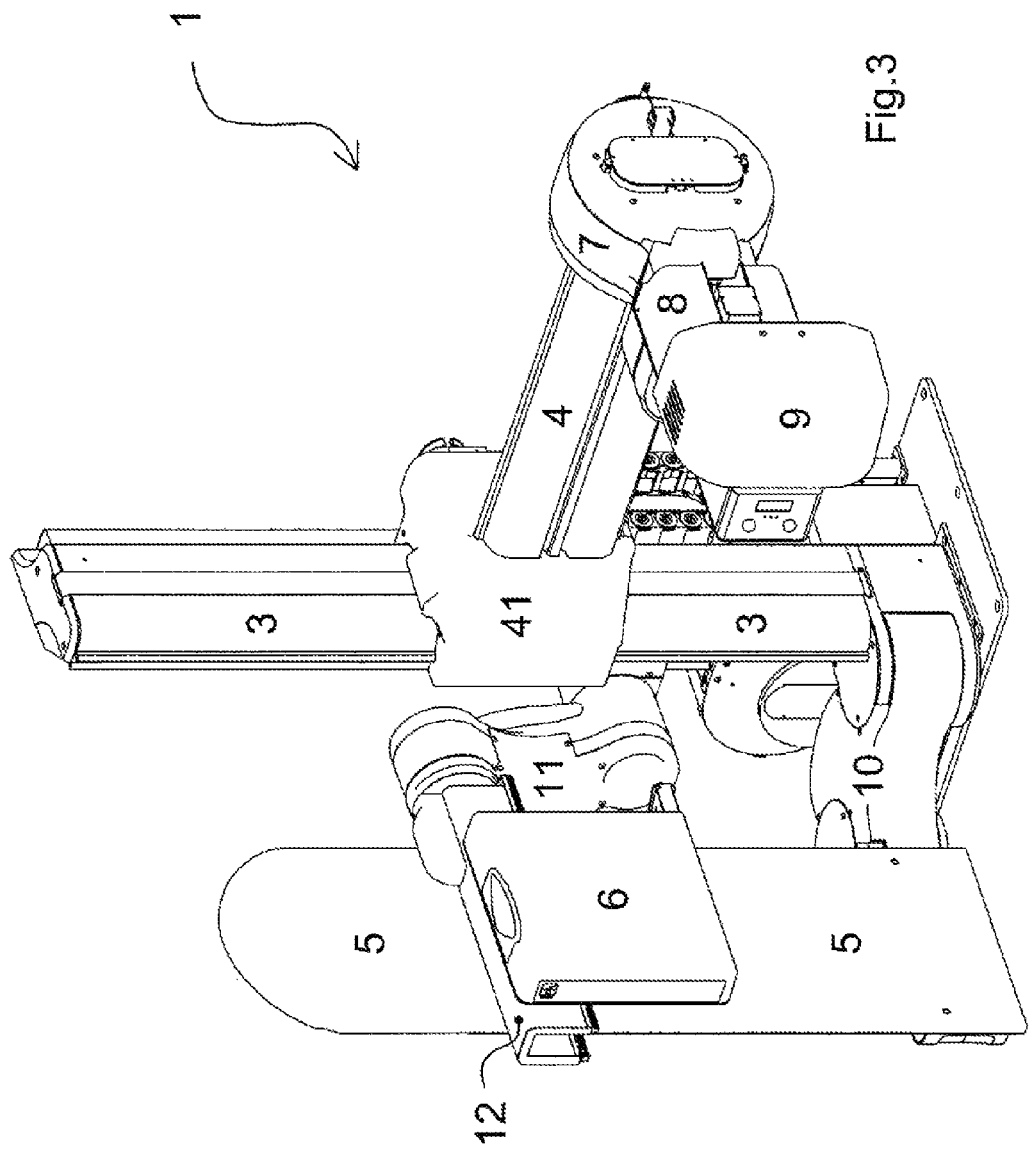
FIG. 3 is a perspective view from the front of one embodiment of the radiological apparatus according to the present invention in a third operating condition.

The first movement is the rotation of the chassis 3 relative to the base 2 about a horizontal axis of rotation transversally to the axis of the chassis column 3; to understand this first movement, reference can be made to FIG. 1 and FIG. 3, for instance; in FIG. 1 the chassis 3 is horizontal, while in FIG. 3 it is vertical.

Figure 5:
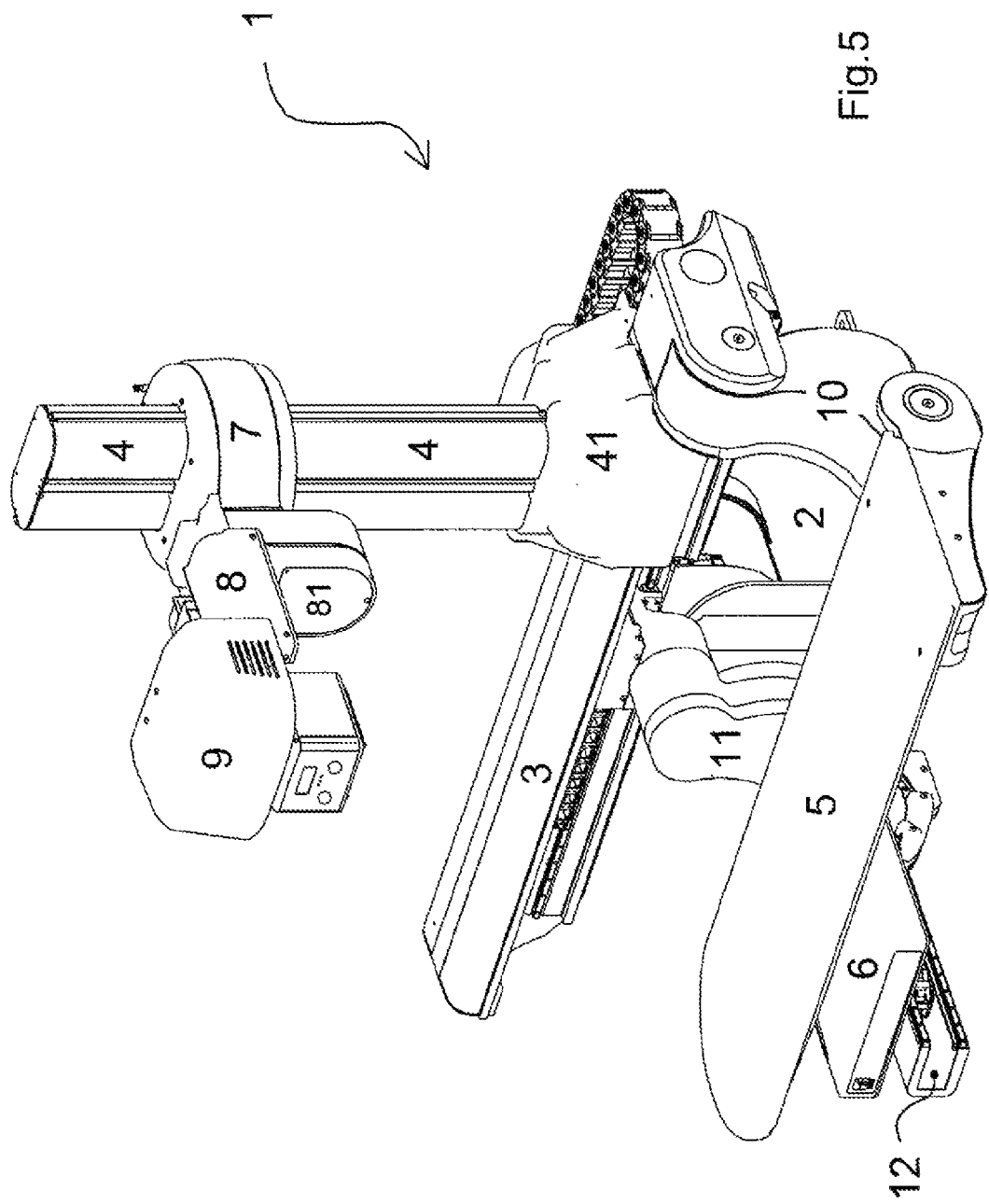
FIG. 5 is a perspective view from the front of one embodiment of the radiological apparatus according to the present invention in a fifth operating condition.

The second movement is the translation of the stand 4 relative to the chassis 3 in a direction parallel to the axis of the chassis column 3; in the example in the figure, this is achieved by means of the slide 41; to understand this second movement, reference can be made to FIG. 1 and FIG. 5, for instance; in FIG. 1 the stand 4 is in the centre of the chassis 3, while in FIG. 5 it is at one end.

The third movement is the translation of the patient bed 5 relative to the chassis 3 in a direction perpendicular to the axis of the chassis column 3; to understand this third movement, reference can be made to FIG. 1 and FIG. 5, for instance; in FIG. 1 the bed 5 is on a level with the chassis 3, while in FIG. 5 it is much lower, near the floor. This movement is achieved by means of the rotation of the arm 10 (in fact the translation is obtained by means of two inverse rotations).

Figure 2:
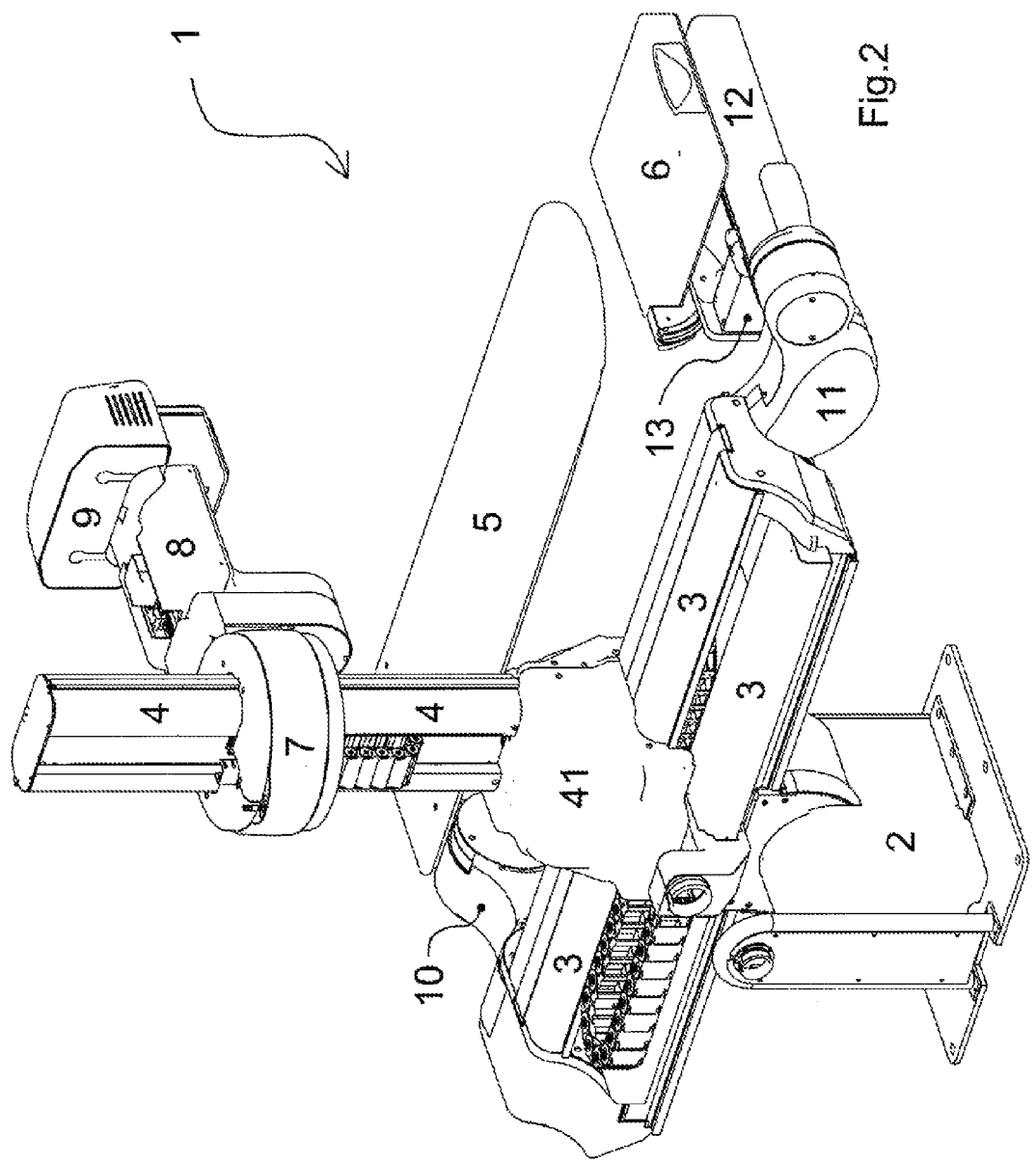
FIG. 2 is a perspective view from the rear of one embodiment of the radiological apparatus according to the present invention in a second operating condition.

The fourth movement is the translation of the X-ray detector 6 relative to the chassis 3 in a direction parallel to the axis of the chassis column 3; to understand this fourth movement, reference can be made to FIG. 1 and FIG. 2, for instance; in FIG. 1 the detector 6 is at the centre of the chassis 3 (and of the patient bed 5), while in FIG. 2 it has moved longitudinally to beyond one end of the chassis 3 (and of the patient bed 5). This movement is achieved by means of the translation of the arm 11.

The fifth movement is the translation of the X-ray detector 6 relative to the chassis 3 in a first direction perpendicular to the axis of the chassis column 3; to understand this fifth movement, reference can be made to FIG. 1 and FIG. 5, for instance; in FIG. 1 the detector is on a level with the chassis 3, while in FIG. 5 it is far lower, near the floor. This movement is achieved by means of the rotation of the arm 11 (in fact the translation is obtained by means of two inverse rotations).

The sixth movement is the translation of the X-ray detector 6 relative to the chassis 3 in a second direction perpendicular to the axis of the chassis column 3; to understand this sixth movement, reference can be made to FIG. 1 and FIG. 4, for instance; in FIG. 1 the detector 6 is near the chassis 3 (under the patient bed 5), while in FIG. 4 it has moved laterally away from the chassis 3 (to beyond the patient bed 5) (and it has also been rotated). This movement is achieved by means of the translation of the slide 13.

In the example in the figures, the translatory directions of the fifth and sixth movements are perpendicular to one another.

The seventh movement is the rotation of the X-ray detector 6 relative to the chassis 3 about an axis of rotation parallel to the axis of the chassis column 3; to understand this seventh movement, reference can be made to FIG. 1 and FIG. 4, for instance; in FIG. 1 the detector 6 is horizontal (under the patient bed 5), while in FIG. 4 it is vertical (alongside the patient bed 5). This movement is achieved by means of the rotation of the detector 6 by the slide 13.

The eighth movement is the rotation of the X-ray detector 6 relative to the chassis 3 about an axis of rotation perpendicular to the axis of the chassis column 3; to understand this eighth movement, reference can be made to FIG. 1 and FIG. 3, for instance; in FIG. 1 the detector 6 is horizontal (under the patient bed 5), while in FIG. 3 it is vertical (opposite the patient bed 5). This movement is achieved by means of the rotation of the shaft 12.

The ninth movement is the translation of the slide 7 relative to the stand 4 in a direction parallel to the axis of the stand column 4; to understand this ninth movement, reference can be made to FIG. 1 and FIG. 4, for instance; in FIG. 1 the slide 7 is midway along the stand 4, while in FIG. 4 it is at the lower end of the stand 4.

The tenth movement is the rotation of the arm 8 relative to the slide 7 about an axis of rotation parallel to the axis of the stand column 4; to understand this tenth movement, reference can be made to FIG. 1 and FIG. 4, for instance; in FIG. 1 the arm 8 is perpendicular to the chassis 3, while in FIG. 4 it is parallel to the chassis 3. This movement is achieved by means of the rotation of the ring 72 around the body 70.

The eleventh movement is the rotation of the arm 8 relative to the slide 7 about an axis of rotation perpendicular to the axis of the stand column 4; to understand this eleventh movement, reference can be made to FIG. 1 and FIG. 4, for instance; in FIG. 1 the appendage 81 of the arm 8 and the appendage 71 of the slide 7 are parallel, while in FIG. 4 they are orthogonal. This movement is achieved by means of the rotation of the appendage 81 of the arm 8 relative to the appendage 71 of the slide 7.

The twelfth movement is the translation of the X-ray emitter 9 relative to the arm 8 in the direction of the arm 8; to understand this twelfth movement, reference can be made to FIG. 4, for instance; the considerable distance between the appendage 81 of the arm 8 and the emitter 9 is particularly evident in this figure—this distance can be reduced by means of said translation.

In actual fact, there is a thirteenth movement, which is the translation of the chassis 3 relative to the base 2. In the present embodiment, however, said movement is connected to the rotation of the chassis 3 relative to the base 2 and is only used to prevent the chassis 3 from coming into contact with the floor when it rotates and moves, for instance, from a horizontal position (FIG. 1) to a vertical position (FIG. 3).

The radiological apparatus according to the present invention enables a plurality of positions and movements; said positions and movements are useful before, during and after the radiological examinations. In short, it is the apparatus that moves around the patient, not the patient around the apparatus.

The positioning and movement of the X-ray detector is extremely variable. The detector can be placed behind the patient bed (as shown in FIG. 1) or in front of the patient bed (as shown in FIG. 3); the detector can therefore also be positioned directly in contact with the patient. The detector can be positioned behind the patient (as shown in FIG. 1) or alongside the patient (as shown in FIG. 4), and even tilted in any spatial direction.

Its positioning in front of and behind the patient bed can be achieved, in the embodiment shown in the figures, thanks to the fact that the detector 6 can be displaced longitudinally until it comes to be entirely beyond one longitudinal end of the patient bed 5 (as shown in FIG. 2); in this extreme position, the rotation of the arm 11 then enables the detector 6 to be positioned above or below the patient bed 5 with no interference between the parts of the apparatus, and between the patient bed and the detector in particular.

Its positioning alongside the patient can be achieved, in the embodiment shown in the figures, thanks to the fact that the detector 6 can be displaced laterally until it comes to be entirely beyond one lateral end of the patient bed 5 (as shown in FIG. 4) due to the sliding of the slide 13 on which the detector 6 is mounted; in this extreme position, the mechanism for the rotation of the slide 13 (located on its right end) can make the detector 6 rotate with no interference between the parts of the apparatus, and between the patient bed and the detector in particular.

It is also possible to ensure that, when the detector 6 has moved completely beyond the lateral end of the patient bed 5, the detector 6 and the patient bed 5 translate reciprocally in a direction perpendicular to the chassis 3, remaining (substantially) parallel to one another, so that the upper surface of the detector 6 is aligned with or exceeds that of the patient bed 5 (e.g. by a few centimeters); the detector 6 alone or the bed 5 alone, or both, can be displaced, but it is preferably the bed 5 that is displaced (bringing it closer to the shaft 12 and inserting it between the slide 13 and the chassis 3); with reference to FIG. 4, this means that the upper surface of the detector 6 can come to be aligned with or slightly higher than that of the patient bed 5; this facilitates examinations involving direct contact between patient and detector in a horizontal position (e.g. for an arm or a hand) and/or examinations in which the patient remains lying on a wheel-mounted stretcher bed, which is simply juxtaposed to the radiological apparatus, without transferring the patient onto the patient bed; it is naturally necessary to shape the arm 11 and/or the shaft 12 and/or the slide 13 suitably in order to enable this minimal translation with no collisions or obstructions.

The radiological apparatus 1 shown in the figures and as described above is the best embodiment of the present invention and is capable of twelve independent movements. In other embodiments, one or more of the above-described movements may be omitted and/or may not be independent.

All twelve movements are motorized in the apparatus 1. According to other embodiments, one or more of the movements may also be manually operated.

Either a static or a dynamic X-ray detector can be mounted in the apparatus 1; the use of a dynamic detector in such a flexible apparatus increases its diagnostic potential enormously. It is preferable to use large "flat panel" detectors.

It is advantageous to provide for the X-ray emitter to have a variable emission aperture, and particularly for it to be adjustable so as to cover only a part (e.g. a circular, oval, square or rectangular portion) of the sensitive surface of the X-ray detector or, in other words, for the radiogenic field to be variable; this reduces the emissions in the case of examinations involving small parts of the body instead of the whole sensitive surface of the X-ray detector (e.g. in the case of examining a part of an arm or hand, or in the case of paediatric X-rays). As regards this latter feature, in particular (i.e. a variable radiogenic aperture/field), it is advantageous for the axes of the emitter and detector to be movable further apart or closer together, while remaining (substantially) parallel to one another, thanks to the mechanisms of the radiological apparatus associated with the X-ray emitter and/or X-ray detector; the axis of the emitter can therefore be centred on a specific point of a part of the body (and thus produce excellent images) irrespective of whether said part of the body has been positioned up against or in line with the axis of the detector; in other words, it is not necessary to make the patient change position.

A very useful flexible feature of the X-ray emitter is related to its collimator, and particularly to the opportunity to rotate the collimator, especially through ±45°.

The opportunity to move the patient bed a considerable distance away from the X-ray detector (e.g. laterally and/or vertically) considerably facilitates the use of the radiological apparatus according to the present invention with the patient lying on a wheel-mounted stretcher bed and therefore avoids the need to transfer the patient onto the patient bed of the apparatus; in fact, there is plenty of space to allow for the stretcher bed to be moved and positioned very freely without it coming into contact and/or interfering with the parts of the apparatus.

An electronic control unit (of the computer-operated and suitably programmed type) is typically provided in the radiological apparatus according to the present invention, generally designed to govern the whole apparatus and, in particular, to control the various movements of its parts on the basis of user commands and/or depending on the examinations being conducted.

Generally speaking, the movements are controlled by the general program for controlling the apparatus as a function of user commands and/or depending on the X-rays to obtain, but also in order to avoid any collisions or interferences between the various movable parts of the apparatus. To guarantee an even greater safety, especially in the light of the large number of independent movements that the apparatus according to the present invention is capable of achieving, an independent, self-contained program is provided (for the best embodiments) that has the sole purpose of monitoring the movements underway, instant by instant, and preventing any collisions or interferences.

In addition to the standard operations of a normal radiological apparatus, the electronic control unit is complete with a user interface that enables preset functional parameters to be input; this option is particularly useful in view of the great flexibility of the apparatus. These preset parameters enable X-rays to be completed correctly and rapidly (be they static or dynamic) and they are input by means of a dedicated software.

In the light of the above description and attached drawings, it will be clear to a person skilled in the art that the radiological apparatus according to the present invention has a highly flexible functionality sufficient to meet a variety of clinical and diagnostic needs.

The invention claimed is:

1. A radiological apparatus comprising:
a base adapted to be laid on a floor,
a chassis that is a column-shape chassis with a chassis column having an axis of the chassis column mounted on the base,
a stand that is a column-shape stand with a stand column having an axis of the stand column mounted on the chassis,
a patient bed mounted on the chassis,
an X-ray detector mounted on the chassis, a slide mounted on the stand,
an arm mounted on the slide,
an X-ray emitter mounted on the arm,
- wherein the axis of the chassis column and the axis of the stand column are perpendicular to each other, and comprising a plurality of further mechanisms adapted to provide a plurality of movements,
- wherein said plurality of further mechanisms are adapted to provide at least the plurality of movements which includes:
  - translation of said X-ray detector relative to said chassis in a first direction perpendicular to said axis of the chassis column; and
  - translation of said slide relative to said stand in a direction parallel to said axis of the stand column,
  - wherein translation of said X-ray detector relative to said chassis is independent of translation of said slide relative to said stand.

2. The radiological apparatus according to claim 1, wherein said plurality of further mechanisms are adapted to provide at least a plurality of a number of following movements, the number of following movements comprising:
- a first movement defined as rotation of the chassis relative to the base about a horizontal axis of rotation perpendicular to the axis of the chassis column,
- a second movement defined as translation of the stand relative to the chassis in a direction parallel to the axis of the chassis column,
- a third movement defined as translation of the patient bed relative to the chassis in a direction perpendicular to the axis of the chassis column,
- a fourth movement defined as translation of the X-ray detector relative to the chassis in a direction parallel to the axis of the chassis column,
- a fifth movement recited in claim 1 as translation of said X-ray detector relative to said chassis in a first direction perpendicular to said axis of the chassis column,
- a sixth movement defined as translation of the X-ray detector relative to the chassis in a second direction perpendicular to the axis of the chassis column,
- a seventh movement defined as rotation of the X-ray detector relative to the chassis about an axis of rotation parallel to the axis of the chassis column,
- an eighth movement defined as rotation of the X-ray detector relative to the chassis about an axis of rotation perpendicular to the axis of the chassis column,
- a ninth movement recited in claim 1 as translation of said slide relative to said stand in a direction parallel to said axis of the stand column,
- a tenth movement defined as rotation of the arm relative to the slide about an axis of rotation parallel to the axis of the stand column,
- an eleventh movement defined as rotation of the arm relative to the slide about an axis of rotation perpendicular to the axis of the stand column,
- a twelfth movement defined as translation of the X-ray emitter relative to the arm in the direction of the arm.

3. The radiological apparatus according to claim 2, wherein said plurality of further mechanisms are adapted to provide all of said number of following movements.

4. The radiological apparatus according to claim 2, wherein all of said number of following movements or a plurality thereof are motorized.

5. The radiological apparatus according to claim 2, wherein all said number of following movements or a plurality thereof are independent.

6. The radiological apparatus according to claim 2, further comprising a second arm associated with the patient bed, wherein the patient bed is rotatably mounted on the second arm, and wherein the second arm is rotatably mounted on the chassis and is adapted to provide said third movement.

7. The radiological apparatus according to claim 2, further comprising a third arm associated with the X-ray detector, wherein the X-ray detector is rotatably mounted on the third arm, and wherein the third arm is translatably and rotatably mounted on the chassis and is adapted to provide said fourth movement and said fifth movement.

8. The radiological apparatus according to claim 7, further comprising a shaft mounted on the arm associated with the X-ray detector, wherein the X-ray detector is translatably and rotatably mounted on the shaft so as to provide said seventh movement and said eighth movement.

9. The radiological apparatus according to claim 8, further comprising a second slide associated with the X-ray detector, wherein the second slide is translatably mounted on the shaft, and wherein the X-ray detector is rotatably mounted on the second slide so as to provide said sixth movement and said seventh movement.

10. The radiological apparatus according to claim 1, further comprising an electronic control unit adapted to control said movements according to user's commands.

11. The radiological apparatus according to claim 10, comprising an electronic control unit adapted to control said movements according to examinations to be carried out.

12. The radiological apparatus according to claim 1, comprising an electronic control unit adapted to control said movements according to examinations to be carried out.

* * * * *